(12) United States Patent
Lewis et al.

(10) Patent No.: US 12,195,569 B2
(45) Date of Patent: Jan. 14, 2025

(54) RADIOPAQUE POLYMERS

(71) Applicant: Boston Scientific Medical Device Limited, Galway (IE)

(72) Inventors: Andrew Lennard Lewis, Farnham (GB); Hugh Britton, Gillingham (GB); Yiqing Tang, Guildford (GB); Jonathan Vince, Billingshurst (GB); Koorosh Ashrafi, Purley (GB); Damien Guégan, Lyons (FR)

(73) Assignee: Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 18/317,747

(22) Filed: May 15, 2023

(65) Prior Publication Data

US 2023/0279172 A1    Sep. 7, 2023

Related U.S. Application Data

(62) Division of application No. 17/252,560, filed as application No. PCT/IB2019/055382 on Jun. 26, 2019, now Pat. No. 11,702,498.

(30) Foreign Application Priority Data

Jun. 29, 2018    (GB) ..................... 1810777
Jun. 29, 2018    (GB) ..................... 1810788

(51) Int. Cl.

| | | |
|---|---|---|
| C08F 261/04 | (2006.01) | |
| A61K 9/00 | (2006.01) | |
| A61K 9/16 | (2006.01) | |
| A61K 49/04 | (2006.01) | |
| A61L 24/00 | (2006.01) | |
| A61L 24/04 | (2006.01) | |
| C08G 67/00 | (2006.01) | |

(52) U.S. Cl.
CPC .......... *C08F 261/04* (2013.01); *A61K 9/0024* (2013.01); *A61K 9/1635* (2013.01); *A61K 49/0442* (2013.01); *A61L 24/001* (2013.01); *A61L 24/0015* (2013.01); *A61L 24/046* (2013.01); *C08G 67/00* (2013.01); *A61L 2400/06* (2013.01); *A61L 2430/36* (2013.01)

(58) Field of Classification Search
CPC ....... C08F 8/48; C08F 261/04; A61K 49/0442
See application file for complete search history.

(56) References Cited

U.S. PATENT DOCUMENTS

| | | |
|---|---|---|
| 4,406,878 A | 9/1983 | DeBoer |
| 4,978,713 A | 12/1990 | Goldenberg |
| 5,508,317 A | 4/1996 | Muller |
| 5,583,163 A | 12/1996 | Muller |
| 6,699,920 B1 | 3/2004 | Andros |
| 2016/0228556 A1 | 8/2016 | Hohn et al. |

FOREIGN PATENT DOCUMENTS

| | | |
|---|---|---|
| CN | 105517582 A | 4/2016 |
| CN | 105968244 A | 9/2016 |
| DE | 480866 C | 8/1929 |
| EP | 0436316 A1 | 7/1991 |
| JP | H06345705 A | 12/1994 |
| JP | 3031718 U | 12/1996 |
| JP | 2018145328 A | 9/2018 |
| WO | 9301221 A1 | 1/1993 |
| WO | 9416749 A1 | 8/1994 |
| WO | 9520407 A1 | 8/1995 |
| WO | 0168721 A1 | 9/2001 |
| WO | 200168720 A1 | 8/2004 |
| WO | 2004071495 A1 | 8/2004 |
| WO | 2007085615 A1 | 8/2007 |
| WO | 2007090897 A1 | 8/2007 |
| WO | 2011110589 A1 | 9/2011 |
| WO | 2014152488 A2 | 9/2014 |
| WO | 2015033092 A1 | 3/2015 |
| WO | 2016115023 A1 | 7/2016 |

OTHER PUBLICATIONS

Chemical Abstracts Service Registry No. 944666-93-7, https://www.cas.org/, Entry date Aug. 15, 2007, as cited in the Office Action for Canadian application No. 3,099,365.
Chemical Abstracts Service Registry No. 342429-83-8, https://www.cas.org/, Entry date Jun. 19, 2001, as cited in the Office Action for Canadian application No. 3,099,365.
Mazumdar et al, "Iodine complexes of acid-functionalized poly(vinyl alcohol) hydrogels: synthesis, characterization and release studies", Journal of Polymer Materials, New Delhi, India, vol. 33, No. 1, p. 41-52, 2016.
Brown et al, "Syntheses and Copolymerization of New Water-Soluble Polyiodinated Acrylic Monomers", Makromolekulare Chemie,vol. 6, No. 7, p. 503-507, Jul. 1985.
Ashrafi et al., "Characterization of a Novel Intrinsically Radiopaque Drug-Eluting Bead for Image-Guided Therapy: DC Bead LUMI{TM}", Journal of Controlled Release, Elsevier, Amsterdam, NL, vol. 250, pp. 36-47, Feb. 2017.
Talekar et al., "Nonreductive Deiodination of Ortho-Iodo-Hydroxylated Arenes Using Tertiary Amines", Journal of Organic Chemistry, 70(21), 8590-8593 CODEN: JOCEAH: ISSN: 0022-3263,2005.
Jones et al., "The Role of Substituents and Solvents in Promoting "Medium-Size" Ring-Chain Tautomerism", Journal of Organic Chemistry, vol. 55, No. 12, 01 p. 3891-3896, Jun. 1990.
Wilkinson et al., "The Biological Action of Substances Related to Thyroxine. 3. Substances Derived 6 From 3,5-DIIODO-4-Hydroxybenzaldehyde and Related Compounds", Biochemical Journal,vol. 19, pp. 714-718, 1951.

(Continued)

*Primary Examiner* — James W Rogers
(74) *Attorney, Agent, or Firm* — Seager, Tufte & Wickhem, LLP

(57) ABSTRACT

This invention relates to radiopaque polymers and to their use, particularly in the manufacture of medical devices and in methods of medical treatment, including therapeutic embolization. In particular embodiments the present disclosure relates to a hydrophilic polymer comprising pendent groups which a phenyl ring is substituted with one or more iodine groups and one or more non-iodine groups as described in more detail herein.

19 Claims, 1 Drawing Sheet

(56) References Cited

OTHER PUBLICATIONS

Chou et al., "Studies of the Triplet State of the Proton-Transfer Tautomer in Salicylaldehydes", Chemical Physics Letters, vol. 370, No. 5-6, 21 p. 747-755, Mar. 2003.

Piscopo et al., "Experimental Observations on the Iodination of Phenolic Compounds for the Synthesis of Intermediates of Pharmaceutical Chemical Interest", Bollettino—Societa Italiana Di Biologia Sperimentale, vol. 59, No. 1, pp. 44-50, 1983.

Bougault et al., "Some Halogenated Derivatives of Salicylic Aldehyde. II. Preparation of 3,5-9 :Iiiodoacetylsalicylaldehyde and of the Diacetyl Acetals of 5-bromo and 3,5-Diiodoacetylsalicylaldehyde. Dharmacodynamic data on these compounds", Bulletin De La Societe Chimique De France pp. 630-632, 1949.

Covello et al., "New Synthetic Iodo-Organic Compounds: o-alkoxybenzaldehydes, o-alkyloxyacetophenones, and Iodine-Containing Analogs", Farmaco, Edizione Scientifica, 19(8), 675-87, 1964.

International Search Report and Written Opinion for the International Patent Application No. PCT/IB2019/055382, mailed Oct. 6, 2020, 23 pages.

Horne et al., "The Regiospecific p-Deiodination of 2,4-Di-iodo Phenols; a New Synthesis of Aflatoxin B2", Journal of the Chemical Society, Chemical Communication, vol. 1, p. 39-41, 1990.

Mawad et al., "Elaboration of Radiopaque Iodinated Nanoparticles for in Situ Control of Local Drug Delivery" Biomaterials, vol. 30 pp. 5667-5674, 2009. aaa.

Glasson, "Experimental toxicology of acetyl medicaments" Schweizerische medizinische Wochenschrift, vol. 82, pp. 851-852, 1952.

Piscopo, Eugenio et al: "New synthetic iodine-containing organic compounds. 3,4,5-Triiodosalicylic acid and Derivatives", Rendiconto Dell'Accademia Delle Scienze Fisiche E Matematiche, Naples, Volume Date 1980, 47, 253-62 CODEN: RASFAM; ISSN: 0370-3568, 1981, XP009523109.

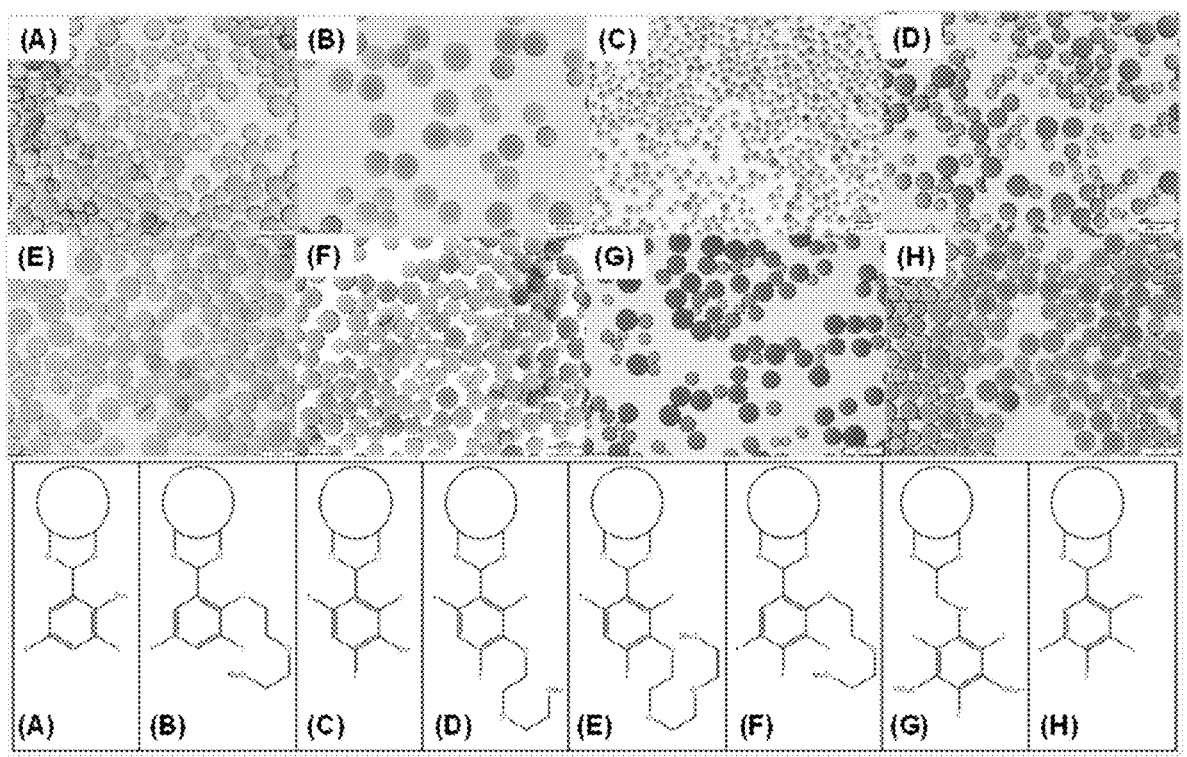

RADIOPAQUE POLYMERS

CROSS-REFERENCE TO RELATED APPLICATIONS

This is a divisional of U.S. patent application Ser. No. 17/252,560, filed on Dec. 15, 2020, titled "Radiopaque Polymers", which is a national stage filing of International Application No. PCT/IB2019/055382, filed Jun. 26, 2019, which claims priority to Great Britain Application No. 1810777.1, filed Jun. 29, 2018, and Great Britain Application 1810788.8, filed Jun. 29, 2018, the disclosures of which are incorporated herein by reference in their entireties for all purposes.

This invention relates to radiopaque polymers and to their use, particularly in the manufacture of medical devices and in methods of medical treatment. The invention particularly relates to radiopaque polymers useful in the field of therapeutic embolisation.

Therapeutic embolisation is a minimally invasive procedure in which a material is introduced into a blood vessel to produce an occlusion in order to slow or stop blood flow. Typically such materials are delivered via a micro-catheter, which is navigated to the target site from a peripheral point such as the leg or wrist. This approach has been useful in the treatment of conditions such as gastrointestinal bleeding, arteriovenous malformations, hypervascular malignant tumours such as hepatocellular carcinoma, benign growths such as uterine fibroids and more recently benign prostate hyperplasia (BPH) amongst others.

Biocompatible microspheres are useful embolic agents because they can be easily delivered to the target site and can be provided in defined size ranges for more predictable embolisation according to the vessel size. Liquid embolics have also found utility in some areas, using materials that are delivered as a liquid, but which gel, solidify or precipitate in situ. Some such systems rely on polymer formation or gelling in situ, whilst others rely on delivery in organic solvents, which rapidly dissipate in the blood leaving behind the embolic material. Liquid embolics have the added advantage that they conform to the vessel wall and, depending on their deposition characteristics, typically form a unified embolus, rather than discrete spheres. Typically embolic materials are synthetic or natural polymers, which are chosen to provide desired properties such as biocompatibility, density, compressibility, flowability, drug loading and ease of catheter delivery. In liquid embolics properties such as flow characteristics in the vessel, speed and predictability of deposition and robustness of the embolus are also important.

Radiopaque polymer microspheres having iodinated groups covalently coupled to the polymer backbone have been proposed (e.g. WO2015/033092). The iodinated groups render these materials visible using X-ray based techniques, but the presence of iodine can lead to suboptimal handling characteristics, such as poor drug loading, poor compressibility and reduced suspension times.

Radiopaque liquid embolics having iodinated groups coupled to the polymer backbone have also been described (e.g. WO2011/110589). As with the polymer microspheres, however, the presence of the iodine alters the physical characteristics of the polymer, leading to poorer handling characteristics such as unpredictable and rapid precipitation, "stringing" of the polymer and other unfavourable handling characteristics. It is desirable therefore to provide improved iodinated polymers that are sufficiently radiopaque to be visible on X-ray, but have improved usability properties.

The present inventors have identified that one or more of these issues can be addressed by the polymers described herein.

In a first aspect, the present invention therefore provides a hydrophilic polymer comprising pendant groups of the formula I.

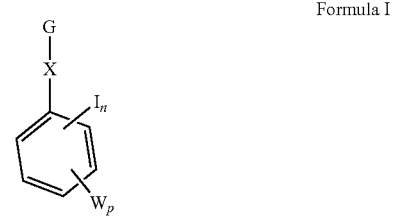

Formula I

Wherein

W is independently selected from —OH, —COOH, —SO$_3$H, —OPO$_3$H$_2$, —O—(C$_{1-4}$alkyl), —O—(C$_{1-4}$alkyl)OH, —O—(C$_{1-4}$alkyl)R$^2$, —O—(C$_2$H$_5$O)$_q$R$^1$—(C=O)—O—C$_{1-4}$alkyl and —O—(C=O)C$_{1-4}$alkyl; or, alternatively W may be a zwitterionic group of the formula —BZ;

wherein —OH, COOH, —OPO$_3$H$_2$ and —SO$_3$H maybe in the form of a pharmaceutically acceptable salt;

X is either a bond or a linking group having 1 to 8 carbons and optionally 1 to 4 heteroatoms selected from O, N and S;

G is a coupling group through which the group of the formula I is coupled to the polymer and is selected from ether, ester, amide, carbonate, carbamate, 1,3 dioxolone, and 1,3 dioxane;

R$^1$ is H or C$_{1-4}$ alkyl;

R$^2$ is —COOH, —SO$_3$H, or —OPO$_3$H$_2$ q is an integer from 1 to 4;

n is an integer from 1 to 4;

p is an integer from 1 to 3;

n+p is from 2 to 5; and wherein —COOH, —OPO$_3$H$_2$ and —SO$_3$H as well as phenolic —OH maybe in the form of a pharmaceutically acceptable salt;

Where W is a zwitterionic group of formula —BZ: B is a bond, or a straight branched alkanediyl, oxyalkylene, alkylene oxaalkylene, or alkylene (oligooxalkylene) group, optionally containing one or more fluorine substituents; and Z is a zwitterionic ammonium, phosphonium, or sulphonium phosphate or phosphonate ester group.

The group Z is zwitterionic and comprises, as the cationic moiety, an ammonium, phosphonium or sulphonium group. Preferably the cation is an ammonium group. The anion of the zwitterion is a phospho moiety. It is generally a phosphate diester, or a phosphonate ester based moiety.

Generally in Z, the anion is closer to B than the cation (non phosphobetaines). However in some zwitterions, the cation is closer to the group B than the anion is (called hereinafter phosphobetaines).

Preferably in non phosphobetaines, Z is a group of the general formula II.

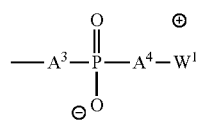

(II)

in which the moieties $A^3$ and $A^4$, which are the same or different, are —O—, —S—, —NH— or a valence bond; preferably —O—, and $W^+$ is a group comprising an ammonium, phosphonium or sulphonium cationic group and a group linking the anionic and cationic moieties which is preferably a $C_{1-12}$ alkanediyl group, preferably in which $W^{1+}$ is a group of formula:

—$W^2$—$N^+R^4_3$,—$W^2$—$P^+R^5_3$,—$W^2$—$S^+R^5_2$, or
—$W^2$—$Het^+$; in which:

$W^2$ is alkanediyl of 1 or more, preferably 2-6 carbon atoms optionally containing one or more ethylenically unsaturated double or triple bonds, di substituted-aryl (arylene), alkylene arylene, arylene alkylene, or alkylene aryl alkylene, cycloalkanediyl, alkylene cycloalkyl, cycloalkylalkylene or alkylene cycloalkyl alkylene, which group $W^1$ optionally contains one or more fluorine substituents and/or one or more functional groups; and either the groups $R^4$ are the same or different and each is hydrogen or alkyl of 1 to 4 carbon atoms, preferably methyl, or aryl, such as phenyl, or two of the groups $R^4$ together with the nitrogen atom to which they are attached form an aliphatic heterocyclic ring containing from 5 to 7 atoms, or the three groups $R^4$ together with the nitrogen atom to which they are attached form a fused ring structure containing from 5 to 7 atoms in each ring, and optionally one or more of the groups $R^4$ is substituted by a hydrophilic functional group, and the groups $R^5$ are the same or different and each is $R^4$ or a group $OR^4$ where $R^4$ is as defined above; and Het is an aromatic nitrogen-, phosphorus- or sulphur-, preferably nitrogen-, containing, ring, for example pyridine.

Compounds in which Z is of the general formula in which $W^+$ is $W^1N^+R^4_3$ may be made as described in WO9301221. Phosphonium and sulphonium analogues are described in WO9520407 and WO9416749. Compounds in which Z is of this general formula in which $W^{1+}$ is $W^2N^+R^4_3$ are preferred.

Generally a Z-group of the formula II has the preferred general formula III

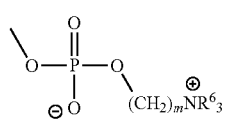

(III)

where the groups $R^6$ are the same or different and each is hydrogen or $C_{1-4}$ alkyl, and m is from 1 to 4, in which preferably the groups $R^6$ are the same, and preferably methyl. A particularly preferred example of this W group is the phosphorylcholine group:

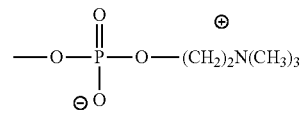

In phosphobetaine based groups, Z may have the general formula IV

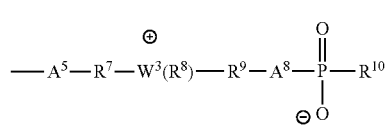

(IV)

in which
$A^5$ is a valence bond, —O—, —S— or —NH—, preferably —O—;
$R^7$ is a valence bond (together with $A^5$) or alkanediyl, —C(O)alkylene- or —C(O)NH alkylene preferably alkanediyl, and preferably containing from 1 to 6 carbon atoms in the alkanediyl chain;
$W^3$ is S, $PR^8$ or $NR^8$;
the or each group $R^8$ is hydrogen or alkyl of 1 to 4 carbon atoms or the two groups $R^8$ together with the heteroatom to which they are attached form a heterocyclic ring of 5 to 7 atoms;
$R^9$ is alkanediyl of 1 to 20, preferably 1 to 10, more preferably 1 to 6 carbon atoms;
$A^6$ is a bond, NH, S or O, preferably O; and
$R^{10}$ is a hydroxyl, $C_{1-12}$ alkyl, $C_{1-12}$ alkoxy, $C_{7-18}$ aralkyl, $C_{7-18}$-aralkoxy, $C_{6-18}$ aryl or $C_{6-18}$ aryloxy group.

Compounds comprising a group of the general formula IV may be made by methods as described in JP03031718B, in which an amino substituted compound is reacted with a phospholane.

In compounds comprising a group of the general formula IV, it is preferred that
$A^5$ is a bond;
$R^7$ is a $C_{2-6}$ alkanediyl;
$W^3$ is $NR^8$, in which each $R^8$ is $C_{1-4}$ alkyl;
$R^9$ is $C_{2-6}$ alkanediyl;
$A^6$ is O; and
$R^{10}$ is $C_{1-4}$ alkoxy.

In phosphobetaines, such as those with groups of the formula II and II, and non phosphobetaines such as those with groups of the formula IV, B is preferred to be a bond, a $C_{1\,to\,6}$ branched or non branched alkanediyl group such as a methylene, ethylene propylene or butylene group, or a branched or non branched $C_{1-6}$ oxyalkylene group such as oxymethylene oxyethylene, oxypropylene or oxybutylene groups.

The invention provides a means to render a wide variety of polymers radiopaque. Preferably the polymer is a hydrophilic polymer, since such polymers are generally more biocompatible.

The polymer is typically selected from the group consisting of: acrylates, acrylamides, acrylics, acetals, allyls, polysaccharides, methacrylates, polyamides, polycarbonates, polyesters, polyethers, polyimides, polyolefins, polyphosphates, polyurethanes, silicones, styrenics, and vinyls, or combinations and/or copolymers thereof. Preferably the polymer comprises monomers selected from: vinyl alcohols, ethylene or propylene glycols, acrylates methacrylates, acrylamides or methacrylamides.

Exemplary hydrophilic polymers suitable for the iodinated polymers include polyvinyl alcohol, acrylates and methacrylates, and their salts, carboxymethylcellulose, hydroxyethylcellulose, polyacrylic acid, polymethacrylic acid, polymethylmethacrylate, polyvinylpyrrolidone, polyacrylamide, polyethylene glycol (PEG), PEG-methacrylate, PEG-methylmethacrylate, Tris(hydroxymethyl)methacrylamide, N,N-methylene-bis-acrylamide, chitosan, alginate, gelatin, starch, or a combination or co-polymer comprising at least one of the foregoing. The polymers may be cross linked.

In a particular embodiment, the polymer comprises or is a polyhydroxylated polymer, i.e. a polymer that comprises repeating units bearing one or more pendant hydroxyls. Preferred polyhydroxylated polymers include those comprising polyol esters of acrylates and methacylates, poly(hydroxyalkylacrylates) and poly(hydroxyalkylmethacrylates), such as poly(hydroxyethylmethacrylate); poly(hydroxyalkylacrylamides) and poly(hydroxyalkyl methacrylamides), such as Tris(hydroxymethyl)methacrylamide; poly(PEGacrylates) and poly(PEGmethacrylates), polymers comprising vinylalcohols such as poly(vinylalcohol) or (ethylene-vinylalcohol) copolymers; and polysaccharides such as starches, chitosans, glycogens, celluloses, such as methyl celluloses, alginates, and polysaccharide gums, such as carageenans, guars, xanthans, gellans, locus bean gums and gum arabics.

Where the polymer is a polyhydroxylated polymer G is preferably selected from ether, ester, carbonate, carbamate, 1,3 dioxolone, and 1,3 dioxane.

In a further embodiment, the polymer may be a poly carboxylated polymer i.e. a polymer that comprises repeating units bearing one or more pendant carboxyl groups. These polymers include, for example, poly acrylic acids poly methacrylic acids and their co-polymers. Where the polymer is a polycarboxylated polymer, G is preferably selected from ester and amide.

Particularly preferred are homopolymers and co-polymers of poly vinylalcohol (PVA).

One type of co-polymer of PVA is a polyvinyl alcohol macromer, having more than one ethylenically unsaturated pendant group per molecule, formed by reaction of the PVA with ethylenically unsaturated monomers. The PVA macromer may be formed, for instance, by providing a PVA polymer, with pendant vinylic or acrylic groups. Pendant acrylic groups may be provided, for instance, by reacting acrylic or methacrylic acid with PVA to form ester linkages through some of the hydroxyl groups. Vinylic group-bearing compounds capable of being coupled to polyvinyl alcohol are described in, for instance, U.S. Pat. No. 4,978,713 and, preferably, U.S. Pat. Nos. 5,508,317 and 5,583,163. Thus the preferred macromer comprises a backbone of polyvinyl alcohol to which is coupled, to an (alk)acrylaminoalkyl moiety. One example of such a polymer comprises a PVA-N-acryloylaminoacetaldehyde (NAAADA) macromer, known as Nelfilcon-B or acrylamide-PVA.

In one preferred embodiment this macromer may be reacted with ethylenically unsaturated monomers optionally bearing a positive or negative charge, such as 2-acrylamido-2-methylpropane sulfonic acid (AMPS). Such polymers and methods of making them are described in WO04071495.

Where the polymer is a polyhydroxylated polymer, the group of the formula 1 is preferably coupled through one or more of the hydroxyl groups. Where the polymer is a polycarboxylated polymer the group of the formula I is coupled through the carboxylate group and G is preferably an ester or an amide.

Where the hydrophilic polymer is, or comprises, PVA, the polymer preferably comprises pendant groups of the formula Ia or Ib, particularly 1b, which are pendant from the PVA.

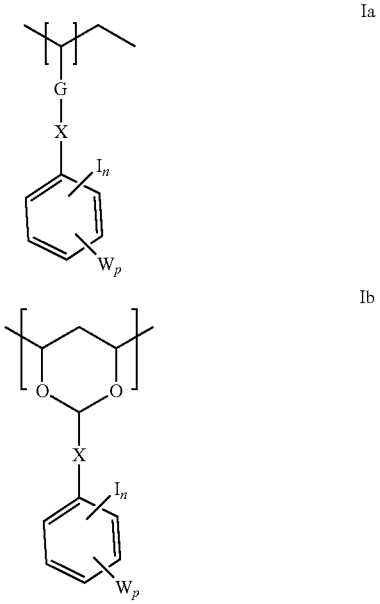

Where G is a coupling group through which the ring is coupled to the polymer through a hydroxyl group and is selected from ether, ester, carbonate and carbamate.

In a particularly preferred embodiment the polymer is a polyhydroxylated polymer which is polyvinyl alcohol or a co-polymer thereof, and wherein the groups of the formula I, Ia or Ib are coupled through hydroxyl groups of the polyvinyl alcohol.

In another particularly preferred embodiment the polymer is a polyhydroxylated polymer which comprises a polysaccharide and wherein the groups of the formula I are coupled through ring or non ring hydroxyl groups of the polysaccharide.

The polymers may be cross-linked. Crosslinking may be covalent or non covalent. Non covalent includes physical crosslinking by entanglement of polymer chains, or by the presence of crystal regions. Ionic cross linking can occur where charged groups on the polymer are cross linked by polyvalent groups carrying the opposite charge. In some cases this can be through di or higher valent metal ions, such as calcium magnesium or barium.

Covalent cross linking can be achieved by any of the established methods to covalently link functional groups on different chains together. If achieved during the polymerisation stage this can be by incorporation of a bifunctional monomer. If post-polymerisation then by a bifunctional species capable of reacting with functional groups on the polymer such as the hydroxyl or carboxyl groups.

The cross linkers may also introduce degradable regions (see for example WO2001/68720), either within the cross-linking molecule or at the termini.

Preferably the cross linked polymer is a hydrogel that is to say, the polymer is water-swellable but water-insoluble. It may comprise greater than 50% and preferably up to 98% water by weight, preferably 60 to 85%.

In addition to any W groups that may be charged, in a preferred embodiment, the polymer may be substituted by groups that are charged at pH7.4. Such groups may carry positive or negative charges, which are able to reversibly bind compounds carrying the opposite charge at physiological pH (pH7.4). A variety of charged groups may be used, including sulphonate, phosphate, ammonium, phosphonium and carboxylate groups; carboxylate and sulphonate are preferred.

W is independently selected from —OH, —COOH, —SO$_3$H, —OPO$_3$H$_2$, —O—(C$_{1-4}$alkyl), —O—(C$_{1-4}$alkyl)OH, —O—(C$_{1-4}$alkyl)R$^2$, —O—(C$_2$H$_5$O)$_q$R$^1$—(C=O)—O—C$_{1-4}$alkyl and —O—(C=O)C$_{1-4}$alkyl;

And preferably from —OH, —COOH, —SO$_3$H, —O—(C$_2$H$_5$O)$_q$R$_1$, —O—(C$_{1-4}$alkyl)R$^2$, (C=O)—O—C$_{1-4}$alkyl, —O—(C=O)C$_{1-4}$alkyl wherein —SO$_3$H, —COOH and phenolic —OH, maybe in the form of a pharmaceutically acceptable salt;

or W may be a group f the formula —BZ

X is preferably either a bond or is a linking group having 1 to 4 carbons and optionally 1 heteroatom selected from O and N; and is more preferably selected from a bond, (C$_{1-4}$)alkylene, (C$_{1-4}$)oxyalkylene, amino(C$_{1-4}$) alkylene. Particular examples include a bond, C$_1$, C$_2$ or C$_3$ alkylene, oxymethyl or oxyethyl, aminomethylene and aminoethylene. Where a linker is present it is particularly a methylene, oxymethylene or amino methylene. Most preferably the ring is directly bonded to the group G, such that X is a bond.

Q is preferably one, two or three; n is preferably 2 or 3 and most preferably 3; R$^1$ is preferably H or methy; and R$^2$ is preferably —COOH or —SO$_3$H.

In one embodiment, the polymer comprises 2 or more versions of the pendant groups of formula 1, each varying from the other in the value for n. There may for example be 2, 3, 4 or more such pendant groups each having a different value for n For example the polymer may comprise pendant groups having 3 iodines and pendant groups having 1 iodine, or pendant groups having 4 iodines and pendant groups having 1 iodine or pendant groups having 2 iodines and pendant groups having 3 iodines, or pendant groups having 1 iodine, pendant groups having 2 iodines and pendant groups having 3 iodines. The proportion of each group may be varied to suit the required properties. In this way the overall hydrophobicity and iodine content/radiodensity of the polymer can be fine tuned to improve the physical properties such as precipitation, density and solubility and robustness of the precipitate in liquid embolics, density compressibility drug loading in microspheres, as well as general catheter handling and delivery properties in either.

The proportion of one iodination value to another can be achieved either by providing a suitable ratio of iodinated phenyl moieties having the appropriate ratio if n values as starting materials, or by mixing polymers having pendant groups with different n values in the appropriate proportion.

Preferably the polymer comprises pendant groups in which the phenyl ring is substituted in one or more of the following ways:

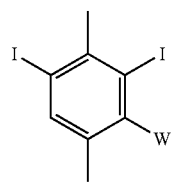

A

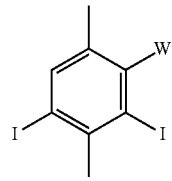

B

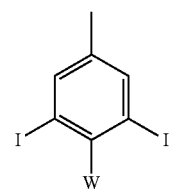

C

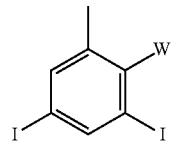

D

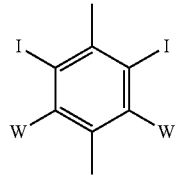

E

Preferred rings include

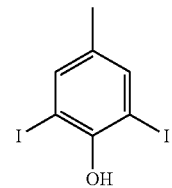

F

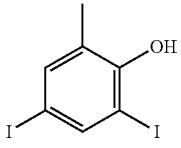

G

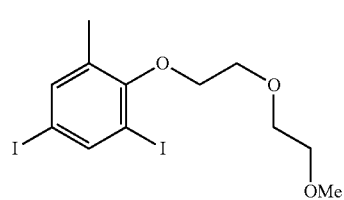

H

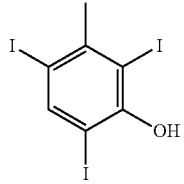

J

-continued

K
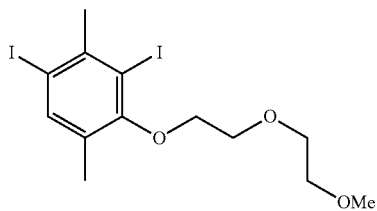

L
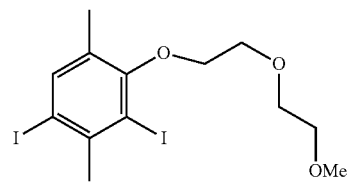

M
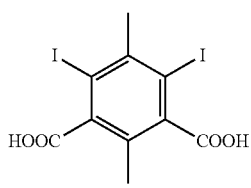

N
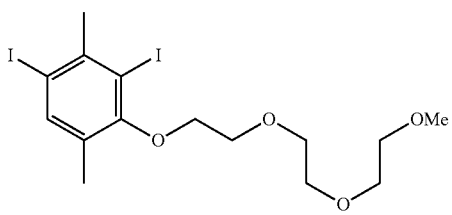

O
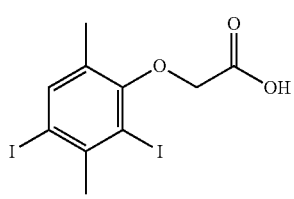

P
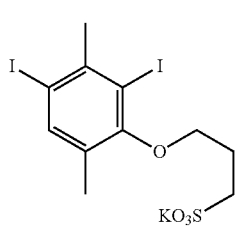

Where, in P, K may be any pharmaceutically acceptable cation, particularly a metal ion such as sodium or potassium The polymers optionally further comprise an active agent, which is preferably reversibly held within the polymer. The agent may be reversibly bound within the polymer by ionic interaction, such as by interaction with positively or negatively charged groups of the polymer as described herein, alternatively, the agent may be held within the polymer by another means such as precipitation (e.g. WO207/085615 or WO2007090897).

The active agent may be a chemotherapeutic agent, an antibody such as cetuximab, trastuzimab and nivolumab, an antibody fragment, a peptide, a low molecular weight protein, or a combination thereof.

Exemplary chemotherapeutic agents include the anthracycline class such as but not limited to doxorubicin, daunarubicin, epirubicin and idarubicin; the camptothecin class such as but not limited to irinotecan, topotecan, and exatecan; the platins such as cisplatin, oxaliplatin, carboplatin and miriplatin; mitomycin C, antimetablites such as 5-fluorouracil; multityrosine kinase inhibitors such as but not limited to sorafenib, sunitinib, regorafenib, brivnb, dasetanib, bosutinib, erlotinib, gefitinib, imatinib and vandetinib, rapamycin or any combination thereof. Where such compounds are ionisable, such compounds may be typically used in their ionic forms.

Radiopacity, or radiodensity, may be varied as required by adjusting the amount of iodine in the polymer. This can be achieved by varying the number of iodines on the ring or by varying the proportion of pendant group to polymer.

Polymers of the invention preferably comprise at least 10 mg of iodine per $cm^3$, preferably 25 $mg/cm^3$, more preferably at least 50 $mg/cm^3$ and especially at least 100 $mg/cm^3$. Where the polymer is water swellable, this figure is measured as mg of iodine per ml of polymer fully swollen in normal saline i.e fully hydrated. Where the polymer is in the form of microspheres, fully hydrated iodine content is expressed as the amount of iodine per ml of fully hydrated beads as a packed volume (e.g., as quantified in a measuring cylinder).

The quantity of iodine in the polymer may be at least 10%, preferably at least 20%, more preferably at least 30% and most preferably at least 35% wt/wt polymer by dry weight. High radiodensity in these polymers can be obtained where iodine is greater than 40% wt/wt dry polymer.

Preferably the polymer of the invention has a radiodenisty of at least 500 HU, preferably at least 1000 HU or 1500 HU more preferably at least 2500 HU and particularly at least 4000 HU. When measured at 65 kV, especially as measured according to Example 12.

The polymer may be biodegradable. Biodegradable polymers herein have linkages that are cleaved by hydrolysis within the body, such that the polymer breaks down. To provide biodegradability, polymers may be provided with a linkage that is hydrolytically cleaveable in the human body, such as an ester group. Such linkages may occur in the backbone or in the cross-linker if present. The polymers may degrade to soluble components over a period of 1 hour to 1 year. Alternatively the polymer may be non biodegradable, such that it will remain present within the body in a stable form for a period greater than 1 year.

The radiopaque polymers of the invention are useful generally in the preparation of implanted medical devices and such devices, comprising polymers described herein provide a further aspect of the present invention. Devices include microspheres, liquid embolics, fiducial markers, tissue-spacing materials, injectable bulking agents, sealants, depots for delivery of active ingredients, wound dressings, and coatings for medical devices e.g. to render them visible under X-ray.

One aspect of the invention provides radiopaque polymers as described herein in the form of microspheres. The polymer microspheres typically have an average largest diameter of up to 2000, um, although the actual size ranges used will depend inter alia on the clinical need. Such particles may be prepared in any sub size range required, for example by sieving. Typical size ranges include 100-300, 300-500, 500-700 and 700-900 um, although smaller size ranges may be advantageous in some circumstances due inter alia, to their more distal embolisation properties. Such smaller size ranges include 70-150 or 40 to 90 um. Typically sizes less than 20 um are avoided due to off target embolisations caused by passage through the capillary bed; thus a lower practical limit is around 20-30 um. Sizes in the range 40 to 700 um, are currently most commonly used in clinical practice. The polymer used may be charged as described herein, so that the microspheres are suitable for loading drugs by ionic interaction.

Microspheres may comprise any polymer described herein, however, in preferred embodiments, the microspheres comprise hydrophilic polymers and particularly polyhydroxylated or polycarboxylated polymers as described herein. In a particularly preferred embodiment, the polymer is a cross linked polyhydroxylated polymer and particularly a cross linked polymer or co-polymer of PVA as described herein, particularly it is a Nelfilcon-B macromer reacted with an ethylenically unsaturated, charged monomer, such as 2-acrylamido-2-methylpropane sulfonic acid (AMPS) or salts thereof (e.g. sodium), particularly as generally described in WO2001/68720, WO0168721 and specifically in example 1 of WO2004/071495.

A further aspect of the invention provides liquid compositions comprising hydrophilic polymers which comprise pendant groups of the formula I. These compositions are suitable as liquid embolic compositions. Preferably these compositions a provided as an injectable liquid composition.

Liquid embolic compositions are compositions where the polymer is delivered to the desired site within the body as a liquid, but forms an embolus in a blood vessel in vivo, particularly where the polymer gels, solidifies or precipitates in situ to form the embolus. Such compositions typically comprise hydrophilic polymers as described herein and a solvent, which may be an aqueous or organic solvent. Preferably the composition comprises a polymer of the formula 1 completely dissolved in the solvent to form a solution of the polymer in the solvent.

Such compositions, intended to precipitate at the target site within the body, typically precipitate in contact with normal saline at 20° C. and compositions in which the polymer precipitates under these conditions provide a further embodiment of the invention. The radiodensity and iodine content of these precipitates is preferably within the ranges preferred for other embodiments of the invention for the polymer.

It is to be noted that the embolus formed typically comprises voids. The figures provided for preferred radiopacities (radiodensities) are for the polymer, rather than for an average across the embolus.

In one approach, hydrophilic polymers as described herein may be provided as a solution in an organic solvent. Typically such solvents are miscible with water. By water miscible is meant that 0.5 ml of the solvent is completely soluble in 1 litre of normal saline at 20° C.

Preferably these solvents are biocompatible. Preferably the solvents are polar aprotic solvents. Preferred solvents are DMSO, DMF, DMPU (N, N'-dimethylpropyleneurea), DMI (1,3-dimethyl-2-imidazolidinone), glycerol, ethyl lactate, NMP and glycofurol (2-(Oxolan-2-yl methoxy)ethanol). In this embodiment, the solvents are preferably selected from DMSO and NMP. In one embodiment, the organic solvent may comprise up to 50% water, preferably up to 25% and most preferably up to 10%

In an alternative approach, the polymers of the formula 1 are dissolved in an aqueous solvent. The aqueous solvent may comprise a biocompatible organic solvent such as those mentioned above. Preferred solvents are selected from DMSO, DMF, DMPU (N, N'-dimethylpropyleneurea), DMI (1,3-dimethyl-2-imidazolidinone), glycerol, ethyl lactate, NMP and glycofurol (2-(Oxolan-2-ylmethoxy)ethanol). Up to 50% v/v of such solvent may be present. The solvents are preferably selected from DMSO and NMP. It is preferred however, that the aqueous solvent is free of organic solvents. In one preferred embodiment the aqueous solvent includes a pharmaceutically acceptable buffer. Examples of such buffers include phosphate, citrate, tromethamine and acetate.

Preferably the liquid composition comprises between 3 and 70% wt/wt, preferably at least 20%. Compositions of 5 to 40%, dissolved polymer or 5 to 25% have useful properties Polymers used in liquid embolics are preferably those comprising vinylalcohols such as poly(vinylalcohol) or ethylene-vinylalcohol polymers and copolymers, as described herein. Most preferably the polymer is a polyvinyl alcohol homopolymer or co-polymer.

The hydrophilic polymers described herein used as liquid embolics, are typically not cross linked.

Preferably the hydrophilic polymer is a non cross linked PVA homopolymer or co-polymer and most preferably a non cross linked PVA homopolymer.

For liquid compositions, the native PVA polymer may be acetylated or non acetylated, typically the level of acetylation in the native PVA is between 50% and 100%, preferably 80% to 100%.

The native PVAs suitable for use in the invention have a weight average molecular weight ranging from 1 KDa to 250 kDa, preferably however the PVA has a weight average molecular weight of at least 20 kDa and preferably at least 40 kDa. Preferred ranges include 40 to 250 kDa and 40 to 200 kDa.

In liquid embolics the hydrophilic polymer may comprise pendant groups of the formula 1a or 1b as described above and reproduced below for ease of reference.

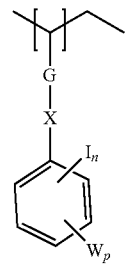

Ia

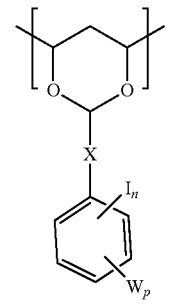

Ib

In addition to the preferences described above for the polymer in general, or for microspheres, when used for liquid embolics:

W is preferably —OH, —COOH, —SO$_3$H, —OPO$_3$H$_2$, —O—(C$_{1-4}$alkyl)R$^2$ and —O—(C$_2$H$_5$O)$_q$R$^1$; wherein —OH, —COOH, —OPO$_3$H$_2$ and —SO$_3$H may be in the form of a pharmaceutically acceptable salt;

In one embodiment, W is selected from —OH, —COOH, —SO$_3$H, —OPO$_3$H$_2$ and —O—(C$_{1-4}$alkyl)R$^2$, preferably —OH, —O—(C$_{1-4}$alkyl)R$^2$ and —COOH, since such polymers form gels, particularly in the presence of polyvalent cations. Such polymers are therefore useful, for example, in the preparation of gel liquid embolics, gel depots of active ingredients, gel fiducial markers and gel based depots of particulate medical devices and active ingredients. These are of particular relevance in the preparation of aqueous liquid embolics, and therefore a further aspect of the present invention provides an aqueous composition comprising polymers of the formula 1. Suitable aqueous cations for forming a gel with polymers of the formula 1 include, for example, calcium, barium, magnesium, strontium and zinc.

Thus one embodiment of the invention provides an aqueous composition comprising polymers described herein, and particularly those suitable for forming gels with polyvalent cations.

A further aspect provides a kit for forming a gel in vivo, comprising an aqueous composition comprising a polymer of the formula 1 and a source of polyvalent cations, such as an aqueous solution thereof.

A further aspect of the present invention provides methods of medical treatment comprising delivering a polymer of the formula I as described herein, to a blood vessel of a subject in need thereof, such as to form an embolus. The polymer may be a microsphere or other particulate form or may be a liquid embolic comprising a polymer as described herein.

Where the polymer is in the form of a liquid embolic, the polymer may be delivered in the form of a composition comprising a solvent that dissipates in the blood stream to provide an embolus, typically an organic solvent as described above, or the polymer is in the form of composition that is caused to form a gel within the vessel so as to form an embolus. In one embodiment the polymer may be delivered separately, sequentially or together with a polyvalent cation that causes the polymer to form a gel. The cation may be delivered in an aqueous solution. Alternatively, gelation can rely on cations present in the blood.

In a further embodiment, the present invention also provides pharmaceutically active ingredients as described herein, for use in a method of medical treatment, wherein the treatment comprises delivering the pharmaceutical active to the patient in the form of an embolic composition comprising the active as described herein and from which the active is eluted during the treatment. The composition may comprise microspheres comprising the pharmaceutical active, or maybe a liquid embolic comprising the active.

The microspheres and liquid embolics described herein may be used to treat a variety of conditions including arteriovenous malformations, gastrointestinal bleeding, filling of aneurysms, treatment of solid tumours, particularly hypervascular tumours, such as those of the liver, prostate, kidney, brain, colon, bone and lung. As well as benign hyperplastic conditions such as prostate hyperplasia or uterine fibroids. The approach can also be used in the treatment of obesity and joint pain.

Where the polymer is a polyhydroxylated polymer, a radiopaque polymer of the formula I where G is an ester linkage, may be prepared by reacting the polyhydroxylated polymer with a compound of the formula VI.

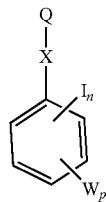

VI

Where Q is a carboxylic acid, an acid halide (such as Cl or Br) or an activated carboxylic acid Where Q is a carboxylic acid the reaction is typically carried out under acid conditions (e.g. sulphuric acid, trifluoroacetic acid, trifluoromethane sulphuric acid, hydrobromic acid in acetic acid, acetic acid & methanesulfonic acid) in an appropriate polar solvent (e.g. DMSO, DMF, NMP).

Where Q is an acid halide the reaction is typically carried out under mild basic conditions in an appropriate polar solvent (e.g. DMSO, DMF, NMP) for example in the presence of a mild base (e.g. pyridine, trimethylamine, lutidine, collidine or imidazole).

Where Q is an activated carboxylic acid, activating agents such as carbodiimides and carbodiidazoles e.g. DCC (N,N'-dicyclohexylcarbodiimide), EDCI (N-(3-dimethylaminopropyl)-N'-ethylcarbodiimide) and HOBt (hydroxybenzotrazole) may be used in polar aprotic solvents, such as DMSO, tetrahydrofuran, ethyl acetate, acetone, dimethylformamide and acetonitrile. The reaction is typically carried out in the presence of a catalytic amount of a base and under anhydrous conditions to achieve activation. The base is typically of moderate strength (pKa of conjugate acid around 10-13) and suitable bases include a variety of pyridines, amines nitrogen heterocycles, triethylamines, N,N-diisopropylethylamine, DMAP and the like.

Coupling iodinated phenyl groups to PVA via an ester linkage, is discussed and exemplified in WO2011/110589, WO2014/152488 and Mawad et al (2009) Biomaterials, 30, 5667-5674, for example.

For the formation of ether linkages, a polyhydroxylated polymer may be reacted with a compound of the formula VI wherein Q is a group selected from halides, such as fluoride, chloride, bromide, iodide; methylsulfonate, methyltoluenesulfonate, trifluoromethane-sulfonate. Q may be for example bromine.

Coupling iodinated phenyl groups to PVA via an ether linkage, is discussed in WO2011/110589.

Where the polymer is a polyhydroxylated polymer having 1,2 or 1,3 diol groups, a radiopaque polymer of the formula I where G is a 1,3 dioxolane or a 1,3, dioxane may be prepared by reacting the polyhydroxylated polymer with a compound of the formula VI wherein Q is a group selected groups capable of forming a cyclic acetal with a diol group, preferably under acidic conditions. In this case Q is preferably selected from the group consisting of aldehydes, acetals, and hemiacetals. Coupling iodinated groups to PVA in this manner, is described in WO2015/033092.

Polymers where G is a carbonate linkage may be prepared by reaction of the polyhydroxylated polymer with a compound of the formula IV where Q is a chloroformate group, such as formula V.

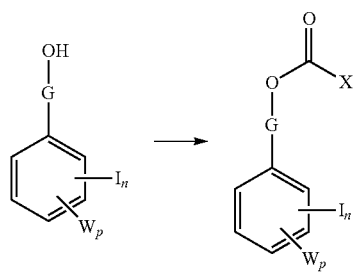

V

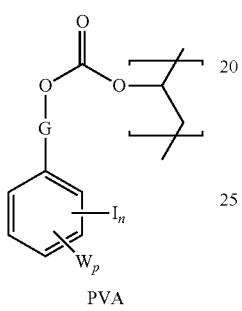

VI

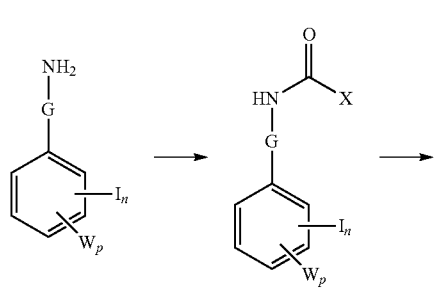

PVA or an isocyanate group such as formula VII:

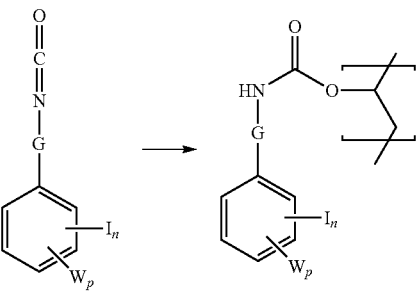

VII

Both of these reactions are mediated by a mild base, such as pyridine, trimethylamine lutidine, collidine or imidazole.

A further aspect of the present invention provides novel starting materials for the preparation of the polymers of the formula I. The present invention therefore provides compounds of the formula VIII:

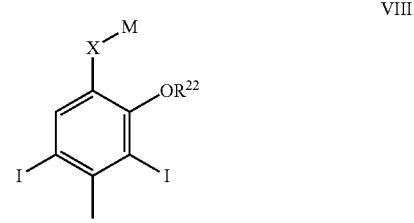

VIII

Where

M is —CHO, —C(OH)OR$^{20}$ or —C(OR$^{21}$)OR$^{20}$; wherein R$^{20}$ and R$^{21}$ are independently selected from C$_{1-6}$ alkyl, preferably R$^{20}$ and R$^{21}$ are methyl; and R$^{22}$ is H, C$_{1-4}$alkyl, C$_{1-4}$hydroxyalkyl, C$_{1-4}$alkyl-R$^2$, —(C$_2$H$_5$O)$_q$R$^1$ or —(C=O) C$_{1-4}$alkyl; or is a group of the formula —BZ;

wherein B is a bond or a straight branched alkanediyl, alkylene oxaalkylene, or alkylene (oligooxalkylene) group, optionally containing one or more fluorine substituents; B is preferably a bond or a C$_{1\ to\ 6}$ branched or non branched alkanediyl group such as a methylene, ethylene propylene or butylene group; and Z is a zwitterionic ammonium, phosphonium, or sulphonium phosphate or phosphonate ester group as described in further detail herein.

R$^1$ is H or C$_{1-4}$ alkyl;

R$^2$ is —COOH, —SO$_3$H, or —OPO$_3$H$_2$; and

Wherein —COOH, —OPO$_3$H$_2$, —SO$_3$H and the phenolic —OH, maybe in the form of a pharmaceutically acceptable salt.

Preferably R$^{22}$ is H, C$_{1-4}$alkyl, C$_{1-4}$alkyl-R$^2$, —(C$_2$H$_5$O)$_q$R$^1$ or —(C=O) C$_{1-4}$alkyl; or is a group —BZ; more preferably R$^{22}$ is H, —(C$_2$H$_5$O)$_q$R$^1$ or —(C=O) C$_{1-4}$alkyl; or is a group —BZ.

The present invention also provides compounds of the formula:

Whilst polymers where G is a carbamate linkage may be prepared by reaction of the a polyhydroxylated polymer with a compound of the formula IV where Q is a carbamoyl chloride group, such as formula VI

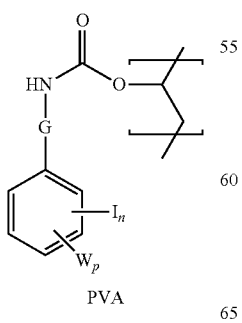

PVA

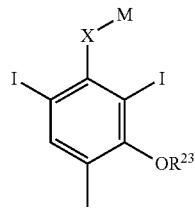

IX wherein
M is —CHO, —C(OH)OR$^{20}$ or —C(OR$^{21}$)OR$^{20}$;
wherein R$^{20}$ and R$^{21}$ are independently selected from C$_{1-6}$ alkyl, preferably R$^{20}$ and R$^{21}$ are methyl; and R$^{23}$ is C$_{1-4}$alkyl, C$_{1-4}$hydroxyalkyl, C$_{1-4}$alkyl-R$^2$, —(C$_2$H$_5$O)$_q$R$^1$ or —(C═O) C$_{1-4}$alkyl; or is a group of the formula —BZ;

wherein B is a bond or a straight branched alkanediyl, alkylene oxaalkylene, or alkylene (oligooxalkylene) group, optionally containing one or more fluorine substituents; B is preferably a bond or a C$_{1\ to\ 6}$ branched or non branched alkanediyl group such as a methylene, ethylene propylene or butylene group; and Z is a zwitterionic ammonium, phosphonium, or sulphonium phosphate or phosphonate ester group as described in further detail herein.

R$^1$ is H or C$_{1-4}$ alkyl;

R$^2$ is —COOH, —SO$_3$H, or —OPO$_3$H$_2$; and

Wherein —COOH, —OPO$_3$H$_2$, —SO$_3$H and the phenolic —OH, maybe in the form of a pharmaceutically acceptable salt.

Preferably R$^{23}$ is C$_{1-4}$alkyl, C$_{1-4}$alkyl-R$^2$, —(C$_2$H$_5$O)$_q$R$^1$ or —(C═O) C$_{1-4}$alkyl; or is a group —BZ; more preferably R$^{23}$ is C$_{1-4}$alkyl-R$^2$, —(C$_2$H$_5$O)$_q$R$^1$ or —(C═O) C$_{1-4}$alkyl.

The present invention also provides compounds of the formula X:

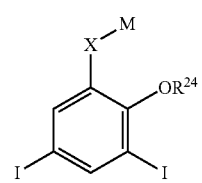

X

Wherein:
M is —CHO, —C(OH)OR$^{20}$ or —C(OR$^{21}$)OR$^{20}$;
wherein R$^{20}$ and R$^{21}$ are independently selected from C$_{1-6}$ alkyl; and R$^{24}$ is H, C$_{1-4}$alkyl, C$_{1-4}$hydroxyalkyl, C$_{1-4}$alkyl-R$^2$, —(C$_2$H$_5$O)$_q$R$^1$ or —(C═O) C$_{1-4}$alkyl; or is a group of the formula —BZ;

wherein B is a bond or a straight branched alkanediyl, alkylene oxaalkylene, or alkylene (oligooxalkylene) group, optionally containing one or more fluorine substituents; B is preferably a bond or a C$_{1\ to\ 6}$ branched or non branched alkanediyl group such as a methylene, ethylene propylene or butylene group; and Z is a zwitterionic ammonium, phosphonium, or sulphonium phosphate or phosphonate ester group as described in further detail herein.

R$^1$ is H or C$_{1-4}$ alkyl;

R$^2$ is —COOH, —SO$_3$H, or —OPO$_3$H$_2$; and

Wherein —COOH, —OPO$_3$H$_2$, —SO$_3$H and the phenolic —OH, maybe in the form of a pharmaceutically acceptable salt.

Preferably R$^{24}$ is H, —(C$_2$H$_5$O)$_q$R$^1$ or —(C═O) C$_{1-4}$alkyl; or is a group —BZ; more preferably R$^{23}$ is H, —(C$_2$H$_5$O)$_q$R$^1$ or —(C═O) C$_{1-4}$alkyl; particularly R$^{24}$ is —(C$_2$H$_5$O)$_q$R$^1$ The present invention also provides compounds of the formula XI.

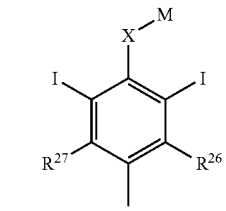

XI

Wherein:
M is —CHO, —C(OH)OR$^{20}$ or —C(OR$^{21}$)OR$^{20}$;
wherein R$^{20}$ and R$^{21}$ are independently selected from C$_{1-6}$ alkyl; preferably methyl and R$^{26}$ and R$^{27}$ are the same or different and each independently selected from the group consisting of —OH, —COOH, —SO$_3$H, —OPO$_3$H$_2$, —O—(C$_{1-4}$alkyl), —O—(C$_{1-4}$alkyl)OH, —O—(C$_{1-4}$alkyl)R$^2$, —O—(C$_2$H$_5$O)$_q$R$^1$—(C═O)—O—C$_{1-4}$alkyl and —O—(C═O)C$_{1-4}$alkyl; or, alternatively W may be a zwitterionic group of the formula —BZ wherein —SO$_3$H, —COOH and phenolic —OH, maybe in the form of a pharmaceutically acceptable salt;

wherein B is a bond or a straight branched alkanediyl, alkylene oxaalkylene, or alkylene (oligooxalkylene) group, optionally containing one or more fluorine substituents; B is preferably a bond or a C$_{1\ to\ 6}$ branched or non branched alkanediyl group such as a methylene, ethylene propylene or butylene group; and Z is a zwitterionic ammonium, phosphonium, or sulphonium phosphate or phosphonate ester group as described in further detail herein.

R$^1$ is H or C$_{1-4}$ alkyl;

R$^2$ is —COOH, —SO$_3$H, or —OPO$_3$H$_2$; and

Wherein —COOH, —OPO$_3$H$_2$, —SO$_3$H and the phenolic —OH, maybe in the form of a pharmaceutically acceptable salt.

Preferably R$^{26}$ and R$^{27}$ are the same or different and each independently selected from the group consisting of —COOH, —SO$_3$H, —OPO$_3$H$_2$, —O—(C$_{1-4}$alkyl)R$^2$, —O—(C$_2$H$_5$O)$_q$R$^1$—(C═O)—O—C$_{1-4}$alkyl; or, alternatively W may be a zwitterionic group of the formula —BZ.

More preferably R$^{26}$ and R$^{27}$ are the same or different and each independently selected from the group consisting of —COOH, and (C═O)—O—C$_{1-4}$alkyl;

One preferred embodiment of XI is a compound of the formula

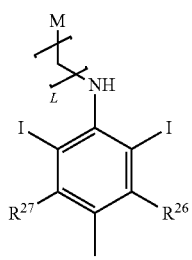

Where L is 1, 2 or 3

The invention will now be described further by way of the following non limiting examples with reference to the figures. These are provided for the purpose of illustration only and other examples falling within the scope of the claims will occur to those skilled in the art in the light of these. All references cited herein are incorporated by reference in their entirety. Any conflict between that reference and this application shall be governed by this application.

FIGURES

FIG. 1 illustrates a selection of microspheres of the invention prepared according to the examples below.

EXAMPLES

Example 1: Synthesis of 3,5-Diiodo-2-(2-(2-methoxyethoxy)ethoxy)benzaldehyde

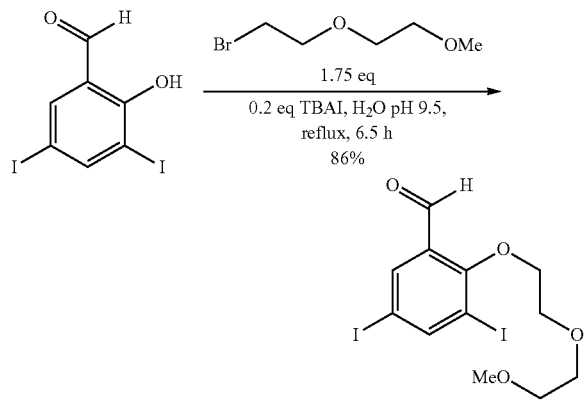

To a HEL PolyBlock8 parallel synthesis 125 ml reactor fitted with a reflux condenser and suspended magnetic stirrer, was added 3,5-diiodosalicylaldehyde (13.9011 g, 37.72 mmol, 1.0 eq) and TBAI (2.7481 mg, 0.802 mmol, 0.2 eq). To this was added water and the pH adjusted to 9.5 with 1M NaOH (total aqueous volume 97 ml). The reactor was set to 500 rpm stirring until full dissolution to give a bright yellow solution and 1-bromo-2-(2-methoxyethoxy)ethane (5.00 ml, 37.17 mmol, 1.0 eq) was added. The reactor zone was set to heat to 120° C. The reaction was monitored by Thin Layer Chromatography (TLC) (30% EA in i-hex) and after 2 hours additional bromide was added (2.50 ml, 18.59 mmol, 0.5 eq). After a further 0.5 hours, the pH was readjusted to 9.5 due to consumption of the bromide. After a further 2 hours additional bromide (1.25 ml, 9.29 mmol, 0.25 eq) were added and the reactor turned down to 50° C. and left to stir overnight. After 19 hours, the resulting suspension was reheated to reflux for 1 hour, cooled to room temperature and transferred to a separating funnel in ethyl acetate (400 ml). The organics were washed twice with saturated sodium bicarbonate, dried with magnesium sulfate, hot filtered from toluene, and recrystallised from toluene/isohexane to give, after filtration and hi-vacuum drying, the desired product as a yellow powder (15.2909 g, 86.4% yield); $\delta_H$ (CDCl$_3$, 500.1 MHz)/ppm; 10.31 (1H, s), 8.31 (1H, d, 2.2 Hz), 8.09 (1H, d, 2.2 Hz), 4.26 (2H, app. t, 4.5 Hz), 3.89 (2H, app. t, 4.5 Hz), 3.67 (2H, app. t, 4.6 Hz), 3.55 (2H, app. t, 4.6 Hz), 3.38 (3H, s); $\delta_C$ NMR (CDCl$_3$, 125.8 MHz)/ppm; 188.71 (CH), 161.55 (q), 152.43 (CH), 137.57 (CH), 131.75 (q), 94.07 (q), 89.19 (q), 75,56 (CH2), 71.90 (CH2), 70.79 (CH2), 70.06 (CH2), 59.13 (CH3).

Example 2: Synthesis of 3-Hydroxy-2,4,6-triiodobenzaldehyde

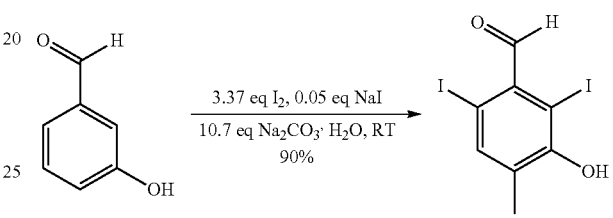

To a 2 L 3-necked round bottomed flask with large oval stirrer bar was added 3-hydroxybenzaldehyde (10.007 g, 81.89 mmol), sodium iodide (0.614 g, 4.09 mmol, 0.05 eq) and sodium carbonate (93.028 g, 877.44 mmol, 10.7 eq), rinsed in with a total of 750 ml of deionised water. When the benzaldehyde had dissolved to give a bright yellow stirred solution, iodine balls (70.008 g, 275.80 mmol, 3.37 eq) was added in 2 portions over 30 minutes and rinsed in with 225 ml of water each time. The reaction is followed by TLC (60% DCM in i-hex) and over 3 hours, the iodine almost completely dissolves resulting in a dark yellow/orange precipitate. The solid was isolated by Buchner filtration and washed with i-hexane to remove any residual iodine. The isolated solid was re-dissolved in warm water (2 L, 45° C.) to give a clear brown solution to which 100 ml of sat. sodium thiosulfate solution were added to reduce any remaining iodine. The pH of the solution was cautiously reduced from 10.2 to 3.26 using 1M HCl (care due to evolution of CO$_2$). The solid was isolated by filtration, washed with water (2×500 ml) and dried in a high vacuum oven at 30° C. to give the desired compound as a yellow solid (37.002 g, 90.3% yield, 97.2% HPLC purity); $\delta_H$ (CDCl$_3$, 500.1 MHz)/ppm; 9.65 (1H, s), 8.35 (1H, s), 6.42 (1H, s); Sc NMR (CDCl$_3$, 125.8 MHz)/ppm; 194.90 (CH), 155.12 (q), 149.77 (CH), 135.69 (q), 88.78 (q), 87.66 (q), 85.70 (q).

Example 3: Synthesis of 2,4,6-triiodo-3-(2-(2-methoxyethoxy)ethoxy)benz aldehyde

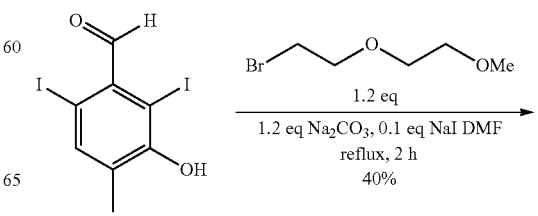

-continued

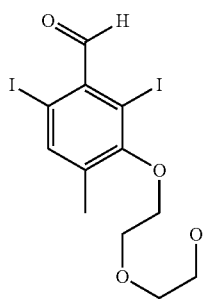

To a flame dried 250 ml 3-necked round bottomed flask under a nitrogen atmosphere containing a stir bar and fitted with a reflux condenser, were added 3-hydroxy-2,4,6-triiodobenzaldehyde (15.627 g, 31.3 mmol, 1.0 eq), sodium iodide (469 mg, 3.13 mmol, 0.1 eq), anhydrous sodium carbonate (3.981 g, 37.6 mmol, 1.2 eq) and anhydrous dimethylformamide (DMF) (160 ml). The suspension was stirred until the aldehyde had completely dissolved, then 1-bromo-2-(2-methoxyethoxy)ethane (6.87 g, 37.5 mmol, 1.2 eq) was added by syringe and the reaction heated to reflux. After 2 hours, TLC analysis (10% EA in i-hex) indicated the start material was consumed and the reaction was cooled to room temperature, transferred to a 250 ml round bottomed flask and evaporated to dryness under high vacuum. The resulting suspension was diluted with 500 ml of ethyl acetate, washed with 3×100 ml 1M NaOH, 2×100 ml sat. brine, decolourised with activated charcoal and dried with magnesium sulfate. The resulting solution was concentrated to dryness, and purified by silica column chromatography (2-20% ethyl acetate in i-hexane) and dried under high vacuum to give the desired compound as a yellow powder (7.556 g, 40.1%); $\delta_H$ (CDCl$_3$, 500.1 MHz)/ppm; 9.65 (1H, s), 8.44 (1H, s), 4.20 (2H, t, 6.4 Hz), 4.01 (2H, t, 6.4 Hz), 3.79 (2H, app. t, 5.8 Hz), 3.60 (2H, app. t, 5.8H), 3.41 (3H, s); $\delta_C$ NMR (CDCl$_3$, 125.8 MHz)/ppm; 194.97 (CH), 159.10 (q), 150.83 (CH), 138.27 (q), 97.06 (q), 95.70 (q), 90.40 (q), 72.47 (CH2), 72.04 (CH2), 70. 89 (CH2), 68.89 (CH2), 59.19 (CH3).

Example 4: Synthesis of 2,4,6-Triiodo-3-(2-(2-(2-methoxyethoxy)ethoxy) ethoxy)benz aldehyde

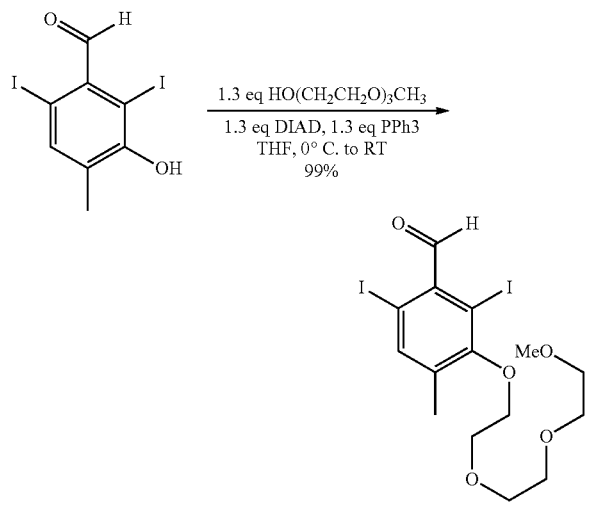

To a flame dried 100 ml 3-necked round bottomed flask containing a stirrer under a nitrogen blanket, was added triphenylphosphine (1.7216 g, 6.502 mmol, 1.3 eq) and anhydrous tetrahydrofuran (THF) (35 ml). The stirring was started and, after full dissolution of the Triphenylphosphine (PPh3), the reactor was cooled to ca 0° C. in an ice-bath. To the colourless solution was added to Diisopropyl azodicarboxylate (DIAD) (1.28 ml, 6.502 mmol, 1.3 eq) dropwise via syringe resulting in a persistent yellow solution. After stirring for 5 minutes, triethylene glycol monomethyl ether (1.04 ml, 6.502 mmol, 1.3 eq) was added dropwise by syringe. After stirring for a further 5 minutes, the 3-hydroxy-2,4,6-triiodobenzaldehyde (2.5077 g, 5.002 mmol, 1.0 eq) was added in one portion resulting in an immediate colour change. The reaction was monitored by TLC (5% Et$_2$O in toluene) and left to stir overnight. The solution was diluted with ether to precipitate triphenylphosphine oxide and then concentrated to dryness. The resulting thick oil was purified by column chromatography (2-10% Et$_2$O in toluene) to give, after concentration and high vacuum drying, the desired product as a yellow powder (3.2077 g, 99% yield, 94.4% HPLC purity); $\delta_H$ (DMSO-D$_6$, 500.1 MHz)/ppm; 9.58 (1H, s), 8.47 (1H, s), 4.08 (2H, t, 4.9 Hz), 3.57-3.53 (4H, m), 3.44 (2H, app. t, 4.8 Hz), 3.24 (3H, s).

Example 5: Synthesis of 3,4,5-Triiodosalicylaldehyde

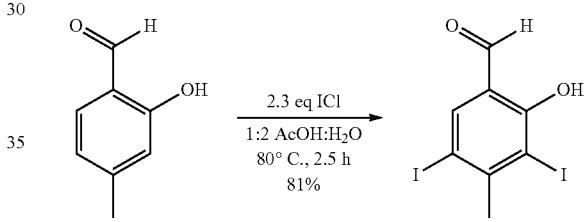

To a 3-necked 2 L round bottomed flask containing a large oval stirrer was added 4-iodo-salicilaldehyde (25.01 g, 100.86 mmol, 1.0 eq) and acetic acid (300 ml). After stirring for 5 mins to allow the solid to dissolve, pre-warmed liquid iodine monochloride (39.11 g, 2.4 eq) was diluted with AcOH (100 ml) and transferred to a dropping funnel on the round bottomed flask. This solution was added over 10 mins. The reactor was then placed in a large silicone oil batch a fitted with a 1 L dropping funnel, thermometer and condenser and set to heat to 80° C. During the heat up, water (700 ml) was slowly added to the solution causing a yellow/orange precipitation. After 20 mins at 80° C., the heating was turned off. After a further 30 minutes the heating bath was removed and the black solution/yellow suspension allowed to cool to room temperature and stirred for 65 hours; the reaction was analysed by TLC (20% EA in iHex). The solid was isolated by Buchner filtration and washed with water (2×500 ml). To remove residual iodine crystals, the solid was repeatedly re-slurried with i-hexane (200 ml) until the i-hexane supernatant was no longer purple. The isolated solid was dried in a hi-vac oven overnight to give the desired product as a yellow crystalline solid (40.84 g, 81% yield, 93.2% pure by HPLC analysis). The product could be further recrystallised to higher purity from acetone:water (9:1); $\delta_H$ (CDCl$_3$, 500.1 MHz)/ppm; 12.15 (1H, s), 9.67 (1H, s), 8.09 (1H, s); $\delta_C$ NMR (CDCl$_3$, 125.8 MHz)/ppm; 194.53 (CH), 159.58 (C), 142.24 (CH), 133.39 (C), 120.87 (C), 101.68 (C), 94.02 (C).

Example 6: Synthesis of 3,4,5-Triiodo-2-(2-(2-methoxyethoxy)ethoxy)benzaldehyde

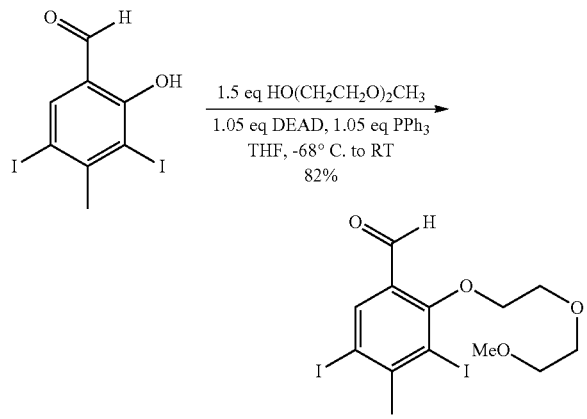

(5 g scale): To a flame dried 3-necked 250 ml round bottomed flask containing a small octagonal stirrer bar under a positive pressure of nitrogen, was added triphenylphosphine (2.76 g, 10.5 mmol, 1.05 eq) and dry THF (70 ml) by syringe. The round bottomed flask was placed in a Dewer bath fitted with a low temperature thermometer and cooled to −68° C. with an ethanol/liquid nitrogen bath. Diethyl azodicarboxylate (1.65 ml, 10.5 mmol, 1.05 eq) was added dropwise by syringe over 1 min and left to stir for 5 mins to give a yellow suspension. Diethyleneglycol mono-methyl ether (1.77 ml, 15 mmol, 1.5 eq) was then added dropwise and left to stir for 5 mins. To this was added solid 3,4,5-triiodosalicylaldehyde (5.00 g, 10.0 mmol, 1.0 eq) in one portion. The initial dark orange/red suspension lightened to give a pale yellow solution which was allowed to stir for 2 hours, monitored by TLC analysis (20% ether in toluene) and left to warm up to room temperature overnight. TLC indicated complete consumption of aldehyde starting material with a clean reaction profile. The resulting solution was transferred to a 500 ml round bottomed flask, diluted with ether (200 ml) and cooled in the freezer. The resulting suspension was filtered through a short silica plug to remove triphenylphosphine oxide and flushed with further ether (200 ml). The resulting solution was concentrated to dryness, and purified by column chromatography eluting with ether in toluene (2-20%) with product fractions concentrated to dryness and dried under high vacuum to give the desired product as a yellow amorphous solid (4.91 g, 82% yield, 96% HPLC purity); $\delta_H$ (CDCl$_3$, 500.1 MHz)/ppm; 10.26 (1H, s), 8.34 (1H, s), 4.22 (2H, t, 4.5 Hz), 3.90 (2H, t, 4.5 Hz), 3.90 (2H, t, 4.6 Hz), 3.55 (2H, t, 4.6 Hz), 3.38 (3H, s); Sc NMR (CDCl$_3$, 125.8 MHz)/ppm;

Example 7: Synthesis of 5-((2,2-Dimethoxyethyl)amino)-2,4,6-triiodoisophthalic acid

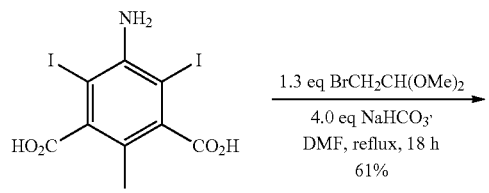

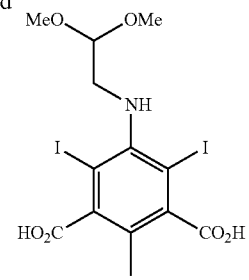

To a flame dried 500 ml round bottomed flask under nitrogen, was added solid 5-amino-2,4,6-triiodoisophthalic acid (46.95 g, 84.03 mmol, 1.0 eq), sodium bicarbonate (28.21 g, 335.8 mmol, 4.0 eq) and DMF (ca 400 ml) via cannula. To the resulting brown solution was added 2-bromo-1,1-dimethoxyethane (13 ml, 110.0 mmol, 1.3 eq) dropwise and the resulting solution heated to reflux for 18 hours. After cooling to room temperature, the majority of DMF was removed by rotary evaporation under vacuum (9 mBar, 55° C.) and the resulting orange solid extracted with ethyl acetate (1 L). This suspension was washed with saturated lithium chloride solution (7×400 ml) to remove residual DMF and salts, dried over magnesium sulfate, filtered and evaporated to dryness. The resulting solid was recrystallised from ethyl acetate, washed with i-hexane and filtered. This process was repeated a total of 3 times and the resulting orange solid dried under high vacuum to give the title compound (33.04 g, 61%, 91.7% HPLC purity). The product could be further purified via silica gel column chromatography (MeOH in DCM, 0-15%) (4.91 g, 82% yield, 96% HPLC purity); $\delta_H$ (CDCl$_3$, 500.1 MHz)/ppm; 8.01 (1H, s), 4.86 (2H, br s), 4.76 (1H, t, 5.5 Hz), 4.37 (2H, d, 5.5 Hz), 3.44 (6H, s); $\delta_C$ NMR (CDCl$_3$, 125.8 MHz)/ppm;

Example 8: Synthesis of Potassium 3-(3-formyl-2,4,6-triiodophenoxy)propane-1-sulfonate

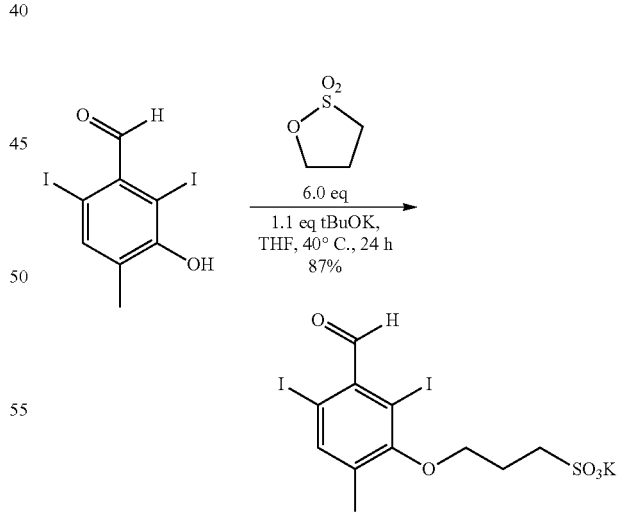

In a 150 mL three-neck round bottom flask, 3-hydroxy-2,4,6-triiodobenzaldehyde (10 g, 20 mmol, 1.0 eq) was dissolved in anhydrous THF(50 ml) by magnetic stirrer. Potassium t-butoxide (2.47 g 22 mmol, 1.1 eq) was mixed with 20 mL of THF and the suspension was added slowly into the flask under nitrogen atmosphere at room temperature, followed by increasing temperature to 40° C. to allow a full dissolution of product. Then sultone (15 g, 120 mmol, 6.0 eq) of was dissolved in 15 mL of THF and the mixture was added slowly to the reaction flask. A precipitation appeared almost immediately. After 3 hours reaction at 40° C., the reaction mixture were poured into 500 mL of ethyl acetate to receive solid raw product. The filtered solid was washed with 100 mL of ethyl acetate, and recrystallized from ethanol. After vacuum drying over 24 hours, the desired product (10.7 g, 80% yield,) was isolated; $\delta_H$ (D$_2$O, 500.1 MHz)/ppm; 2.24-2.34 (m, 2H), 3.12-3.25 (t, 2H), 3.88-4.02 (t, 2H), 8.18-8.25 (s, 1H), 9.42-9.50 (s, 1H) $\delta_C$ NMR (CDCl$_3$, 125.8 MHz)/ppm; Element analysis result: C18.56, H 2.22, S 5.66, 152.31, K 6.27. Cal: C 18.20, H 1.22, S 4.85, 157.68, K 5.92.

Example 9: Preparation of Microspheres

Microspheres were prepared according to Example 1 of WO2004/071495 (high AMPS method). The process was terminated after the step in which the product was vacuum dried to remove residual solvents. Beads were then sieved to provide appropriate size ranges. Beads were either stored dry or in physiological saline and autoclaved. Unless otherwise stated coupling was carried out on batches of microspheres having diameters between 70 and 170 μm and reactions were carried out on dried beads that were swollen in the appropriate solvent prior to use.

Example 10: General Microsphere Coupling Method

To a pre-dried reactor under a nitrogen blanket was added the desired chemical substrate (typically 0.6 eq w.r.t. PVA diol functionalities), anhydrous solvent (typically dimethyl sulfoxide (DMSO) or N-Methyl-2-pyrrolidone (NMP), 30 vol w.r.t. particle mass) and catalyst (typically 2.2 vol w.r.t. particle mass). With stirring, the solution was warmed up to reaction temperature (40-80° C.). Bead micro-particles were then added, rinsed in to the reactor with further anhydrous solvent (typically 5 vol w.r.t. particle mass). The reaction was then stirred under an N$_2$ blanket and the reaction conversion was monitored by High Performance Liquid Chromatography (HPLC) for consumption of the chemical substrate. At a pre-determined time (typically when bead uptake of chemical had ceased), the stirring was switched off and the beads allowed to settle. The supernatant fluid was removed by aspiration through a filter membrane and solvent (typically 35 vol of either 0.5% w/w NaCl in DMSO or NMP) was charged and stirred for up to 10 minutes. The solvent washing was repeated for a total of 5 solvent washes and a further 5 washes with 0.9% saline (typically 50 vol w.r.t. particle mass). The resulting particle suspension was transferred to a 10 ml Schott vial in PBS and autoclaved at 121° C. for 30 mins then cooled to room temperature.

Example 11: Characterization of Radiopaque Microspheres

The dry weight of beads was measured by removing the packing saline and wicking away remaining saline with a tissue. The beads were then vacuum dried at 50° C. overnight to remove water, and the dry bead weight and solid content (w/w %) of polymer were obtained from this. To determine iodine levels per unit volume, settled volume of fully hydrated beads is determined, for example by measuring cylinder, and the beads are then dried and iodine content is determined. The iodine content in dry, beads were measured by elemental analysis according to the Schöniger Flask method.

Example 12: X-Ray Analysis of Individual Radiopaque Beads and Liquid Embolic Polymers Micro-CT was used to evaluate the radiopacity of samples of radiopaque embolic beads prepared according to general example 10 above. The samples were prepared in Nunc cryotube vials (Sigma-Aldrich product code V7634, 48 mm×12.5 mm). The beads were suspended in 0.5% agarose gel (prepared with Sigma-Aldrich product code A9539). The resulting suspension is generally referred to as a "Bead Phantom". To prepare these bead phantoms, a solution of agarose (1%) is first raised to a temperature of approximately 50° C. A known amount of the beads is then added, and the two gently mixed together until the solution starts to solidify or gel. As the solution cools it gels and the beads remain evenly dispersed and suspended within the agarose gel.

Bead phantoms were tested for radiopacity using micro-Computer Tomography (Micro-CT) using a Bruker Skyscan 1172 Micro-CT scanner at the RSSL Laboratories, Reading, Berkshire, UK, fitted with a tungsten anode. Each phantom was analysed using the same instrument configuration with a tungsten anode operating at a voltage of 64 kV and a current of 155 pA. An aluminium filter (500 μm) was used.

For liquid embolic samples, a two part analysis method is used. Initially an interpolated region of interest is created coving the inner tube diameter to include the plug and any void structures then the image is segmented to isolate the polymer from the void structures so as to report polymer radiodensity. The radiodensity in HU was then calculated using the water standard acquired on the same day. Table 1 gives the acquisition parameters.

TABLE 1

| | |
|---|---|
| Software: | SkyScan1172 Version 1.5 (build 14) NRecon version 1.6.9.6 |
| CT Analyser version | 1.13.1.1 |
| Source Type: | 10 Mp Hamamatsu 100/250 |
| Camera Resolution (pixel): | 4000 × 2096 |
| Camera Binning: | 1 × 1 |
| Source Voltage | 65 kV |
| Source Current uA | 153 |
| Image Pixel Size (um): | 3.96 |
| Filter | Al 0.5 mm |
| Rotation Step (deg) | 0.280 |
| Output Format | 8 bit BMP |
| Dynamic Range | 0.000-0.140 |
| Smoothing | 0 |
| Beam Hardening | 0 |
| Post Alignment | corrected |
| Ring Artefacts | 16 |

A small amount of purified MilliQ® water was carefully decanted into each sample tube. Each sample was then analysed by X-Ray micro-computer tomography using a single scan, to include the water reference and the beads. The samples were then reconstructed using NRecon and calibrated against a volume of interest (VOI) of the purified water reference. A region of interest (ROI) of air and water was analysed after calibration to verify the Hounsfield calibration.

Radiodensity was reported in Hounsfield units from line scan projections across the bead. Values used for dynamic range for all samples in NRecon (thresholding): −0.005, 0.13 (minimum and maximum attenuation coefficient).

Table 2 gives the radiodensity, iodine and solid content of microspheres prepared according to general example 10. Radiodensity data are the mean of ten line scans of each individual microsphere. Multiple microspheres were analysed for each preparation.

TABLE 2

| Microsphere prototype | Product | Solid content (mg/ml) | Iodine (% wt/wt Dry) | Iodine (mg/cm³ wet) | Radio-density (HU) |
|---|---|---|---|---|---|
| 1 | | 268.99 | 37.4 | 100.7 | |
| 2 | | 304.8 | 36.4 | 111.0 | 3668 |
| 3 | | 329.9 | 41.4 | 136.6 | |

TABLE 2-continued
| Microsphere prototype | Product | Solid content (mg/ml) | Iodine (% wt/wt Dry) | Iodine (mg/cm$^3$ wet) | Radio-density (HU) |
| --- | --- | --- | --- | --- | --- |
| 4 | 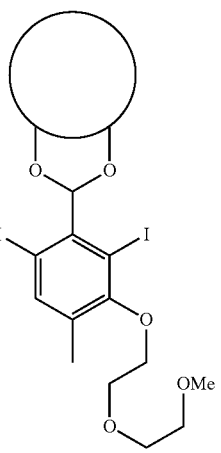 | 368.9 | 40.8 | 150.3 | 4643 |
| 5 | 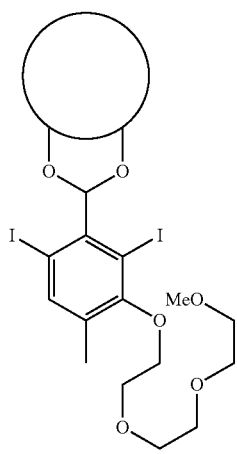 [SMILES: COCCOCCOCCOc1c(C)cc(I)c(C(OC)OC)c1I] | 151.9 | 33.37 | 50.7 | 956 |
| 6 | 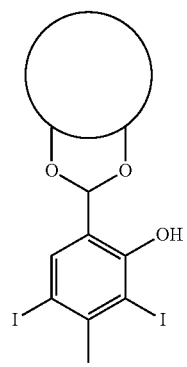 | 245.6 | 46.3 | 113.7 | 3860 |

TABLE 2-continued

| Microsphere prototype | Product | Solid content (mg/ml) | Iodine (% wt/wt Dry) | Iodine (mg/cm$^3$ wet) | Radio-density (HU) |
|---|---|---|---|---|---|
| 7 | (structure: microsphere with acetal linker to 3,5-diiodo-4-methyl-2-(2-(2-methoxyethoxy)ethoxy)phenyl) | 397.9 | 43.6 | 173.4 | 5389 |
| 8 | (structure: microsphere with acetal-CH$_2$-NH linker to 3,5-diiodo-2,6-dicarboxy-4-methylphenyl) | 329.1 | 43.8 | 144.2 | 5368 |

Example 13: General Liquid Embolic Synthesis Conditions

To a pre-dried reactor under a nitrogen blanket was added PVA (typically 5-10 g) and anhydrous solvent (typically DMSO or NMVP, 40 vol w.r.t. PVA mass) and catalyst (typically 2.2 vol w.r.t. PVA mass). The stirred suspension was heated to elevated temperature (ca 90° C.) to dissolve the PVA. When a homogeneous solution had been obtained, the mixture was cooled to the desired reaction temperature (typically 50-80° C.) the desired chemical substrate (typically 0.1 to 0.6 eq w.r.t. PVA diol functionalities) was added. The reaction was then stirred under an N$_2$ blanket and the reaction conversion was monitored by TIPLC for consumption of the chemical substrate. At a pre-determined time (typically when consumption of the chemical substrate had ceased) an anti-solvent was added (typically, acetone, DCM, MeCN or TBME, ca 40 vol) dropwise from a dropping funnel. The supernatant fluid was removed by aspiration through a filter membrane and further reaction solvent (typically 40 vol) was charged and stirred until the solids had fully dissolved. This solvent washing stage was repeated up to 3 times. Then the solid was re-dissolved in reaction solvent, and precipitated by the slow addition of water (typically up to 100 vol). The resulting aggregated solid was removed from the supernatant and homogenised in a blender in water (ca 1l). The suspension was filtered and re-suspended in water (typically 100 vol) and slurried for up to 30 minutes and filtered. The water slurrying was repeated until pH neutral had been obtained, then the damp solids were slurried in acetone (100 vol, 30 mins stir, 2 repetitions), filtered and dried in a high vacuum oven at 30° C. for up to 24 hours.

Example 14: Preparation of Liquid Embolic Prototypes

A sample prototype was prepared in the following fashion: iodinated PVA prepared according to general example 12, was weighed into a 10 ml vial, to which was added the desired solvent (typically DMSO or NMP) such that the overall concentration was in the range 4-20% w/w with a total volume being less than 10 ml. To this, if desired to create ionic liquid embolic species, sodium hydroxide (4M) was added at tis time. The vial containing the thick suspension was then sealed and placed in a sonicator, and sonicated until complete dissolution had occurred (typically ca 4 hours).

Example 15. Preparation of 3,4,5-triiodosalicylaldehyde (TISA)-PVA

To a dry 600 ml HEL (ltd) PolyBLOCK® vessel under a nitrogen blanket, was added DMSO (200 ml, 67 vol) and the stirring initiated at 500 rpm. To this was charged PVA (85-124 kDa, 100% hydrolysed, 3.0051 g) which was rinsed into the reactor with DMSO (10 ml) and the suspension heated to 80° C. (internal probe) until all the solids had dissolved. The solution was then cooled to 60° C. internal and 3,4,5-triiodosalicylaldehyde (3,4,5,-TISA, 6.8140 g, 13.6 mmol, 0.25 eq w.r.t. PVA-1,3-diol units) was charged and rinsed in with DMSO (10 ml). After full dissolution, methanesulfonic acid (6 ml, 2 vol) was added in one portion and the reaction was stirred at 60° C. until HPLC analysis showed consumption of 3,4,5-TISA had halted. The solution was cooled to room temperature and transferred to 2 L glass breaker containing a large stirrer bar to which was added from a dropping funnel, dichloromethane (DCM) (250 ml) then toluene (500 ml). The yellow supernatant was decanted and the resulting solid slowly re-dissolved in DMSO (150 ml) at 50° C. for 1.5 hours. The polymer was precipitated by the slow addition of toluene (500 ml) and the coloured supernatant removed by in-situ filtration. The polymer was re-dissolved in DMSO (150 ml) overnight, then precipitated by the dropwise addition of water (500 ml). The resulting solid was removed, was blended in water to achieve a homogeneous suspension. The pH of the solution was confirmed a pH7, and the solids were isolated by filtration on a Buchner funnel, washed with water (250 ml) and acetone (250 ml) and dried in a hi-vacuum oven at 30° C. overnight to give the desired product as a yellow/white solid (9.1517 g, 93.2% w/w yield).

Table 3 shows yield and iodine content (w/w) for sample liquid embolic preparations prepared according to this general protocol, with varying molecular weight samples of PVA and TISA/PVA ratios.

TABLE 3

| Preparation | MW PVA | Eq. TISA | Conversion | Yield (% w/w) | % $I_2$ (w/w) |
|---|---|---|---|---|---|
| 1 | 85-124 kDa 100% hydrolysed | 0.1 eq | 100% | 88.8% | 28.1% |
| 2 | 85-124 kDa 100% hydrolysed | 0.25 eq | 99.4% | 97.3% | 44.3% |
| 3 | 85-124 kDa 100% hydrolysed | 0.4 eq | 97% | 93.2% | 51.9% |
| 4 | 85-124 kDa 100% hydrolysed | 0.6 eq | 90% | 90.2% | 55.4% |
| 5 | 67 kDa, 88% hydrolysed | 0.6 eq | 57% | 67.4% | 51.8% |

Example 16: Precipitation of Liquid Embolic Under Flow Conditions

A clear detachable tube was attached to a flow system through which PBS was pumped through the detachable tubing using a peristaltic pump to mimic blood flow conditions. A 2.4 Fr catheter was used to deliver the liquid embolic preparation into the detachable tube. As the liquid embolic left the catheter and came into contact with PBS, it precipitated inside the detachable tubing. The length of any precipitate was then measured from the end of the catheter tip. Flow rate and rate reduction were also recorded. The "longest length of advancement" was recorded. If reflux had occurred, its length was also recorded as the "longest length of reflux" (cm). Table 4 records precipitation properties of liquid embolic preparations

TABLE 4

| eq TISA | eq base (per TISA) | Solvent | wt/wt polymer | Longest length of advancement (cm) | Longest length of reflux (cm) | Flow rate reduction (%) |
|---|---|---|---|---|---|---|
| 1 0.1 | | NMP | 8 | 3.5 | 1 | 99.8 |
| 2 0.25 | | NMP | 8 | 4 | 0.5 | 99.7 |
| 1 0.1 | | DMSO | 8 | 4 | 1 | 99.8 |
| 2 0.25 | | DMSO | 8 | 5 | 1 | 99.8 |
| 3 0.4 | | DMSO | 8 | 2.4 | 1.9 | 95.0 |
| | | DMSO | 12 | 3.7 | 1 | 85.5 |
| | | NMP | 8 | 3.5 | 1 | 97.2 |
| | | NMP | 12 | 6 | 0 | 86.5 |
| 4 0.6 | | DMSO | 8 | 4.7 | 1.2 | 90.0 |
| | | DMSO | 12 | 5.5 | 2 | 65.5 |
| | | NMP | 8 | 3.5 | 1.5 | 96.9 |
| | | NMP | 12 | 3.5 | 1.5 | 100.0 |
| 5 0.6 | 0.33 | NMP | 12 | 2.5 cm | 1 cm | 100.0 |
| | 0.66 | | 12 | — | — | — |
| | 0.22 | | 12 | 2.5 cm | 1.5 cm | 100.0 |
| | 0.11 | | 12 | 3.5 | 0.5 | 98.0 |

Example 17: X-Ray Analysis of Precipitated Liquid Embolic Samples

In order to obtain radiopacity measurements for the material, 1 cm sections of precipitated formulations are cut and embedded in warm (55° C.) 100 agarose in a polypropylene capped tube, (such as a Nunc tube) and scanned using Micro-CT according to Example 12. Table 4 illustrates radiopacities of prepared formulations of Example 13

TABLE 4

| TISA Eq | Original Plug Solvent | Concentration | Added (NaOH) | Radiopacity of polymer |
|---|---|---|---|---|
| 0.6 | NMP | 12% (w/w) | 0.11 eq | 4414HU |
| 0.4 | NMP | 12% (w/w) | 0 eq | 3815HU |
| 0.6 | NMP | 12% (w/w) | 0 eq | 4809HU |

The invention claimed is:
1. A hydrophilic polymer comprising pendent groups of the formula I:

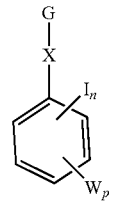

Formula I wherein:
W is independently selected from —OH, —COOH, —SO$_3$H, —OPO$_3$H, —O—(C$_{1-4}$ alkyl), —O—(C$_{1-4}$ alkyl)OH, —O—(C$_{1-4}$ alkyl)R$^2$, —O—(C$_2$H$_5$O)$_q$R$^1$, —(C=O)—O—C$_{1-4}$ alkyl and —O—(C=O)C$_{1-4}$ alkyl, where —OH, —COOH, —O—PO$_3$H and —SO$_3$H may be in the form of a pharmaceutically acceptable salt; or a group —BZ;
B is a bond, or a straight branched alkanediyl, oxyalkylene, alkylene oxaalkylene, or alkylene group, optionally containing one or more fluorine substituents; and Z is an ammonium, phosphonium, or sulphonium phosphate or phosphonate ester zwitterionic group;

X is either a bond or a linking group having 1 to 8 carbons and optionally 1 to 4 heteroatoms selected from O, N and S;

G is a coupling group through which the group of the formula I is coupled to the polymer and is selected from 1,3-dioxolane and 1,3 dioxane;

$R^1$ is H or $C_{1-4}$ alkyl;

$R^2$ is —COOH, —$SO_3H$, or —$OPO_3H_2$ q is an integer from 1 to 4;

n is an integer from 1 to 4;

p is an integer from 1 to 3; and n+p is from 2 to 5.

2. The polymer of claim 1 which is a polyhydroxylated polymer.

3. The polymer of claim 1 which is a co-polymer of polyvinyl alcohol and wherein the groups of the formula I are coupled through hydroxyl groups of the polyvinyl alcohol.

4. The polymer of claim 1 in which n is two or three.

5. The polymer of claim 1 in which the phenyl ring of the group of the formula I is 3,5 diiodinated, 3,4,5 triiodinated or 2,4,6 triiodinated.

6. A polymer according to claim 1 in which p is 1.

7. The polymer of claim 1 in which W is independently selected from —OH, —COOH, —$SO_3H$, —$OPO_3H_2$, —O—($C_{1-4}$ alkyl), —O—($C_{1-4}$ alkyl)OH, —O—($C_{1-4}$ alkyl)$R^2$, —O—($C_2H_5O)_qR^1$, —(C=O)—O—$C_{1-4}$ alkyl and —O—(C=O)$C_{1-4}$ alkyl, where —OH, —COOH, —O—$PO_3H$ and —$SO_3H$ may be in the form of a pharmaceutically acceptable salt, or a group —BZ, wherein B is a bond, a branched or non-branched $C_{1-6}$ alkanediyl group or a branched or non-branched $C_{1-6}$ oxyalkylene group; and Z is a group of formula II

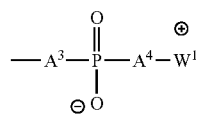

wherein $A^3$ and $A^4$, are the same or different and are selected from —O—, —S—, and —NH—; and —$W^{1+}$ is —$W^2$—$N^+R^4_3$, in which $W^2$ is $C_{1-6}$ alkanediyl and $R^4$ are the same or different and each is hydrogen or $C_{1-4}$ alkyl.

8. The polymer of claim 1 in which W is selected from —OH, —COOH, —$SO_3H$, —$OPO_3H_2$, —O—($C_{1-4}$ alkyl)$R^2$ and —O—($C_2H_5O)_qR^1$; wherein —OH, —COOH, —$OPO_3H_2$ and —$SO_3H$ may be in the form of a pharmaceutically acceptable salt.

9. The polymer claim 1 in which the phenyl ring of the group of the formula I is substituted in one of the following patterns:

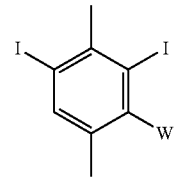
A

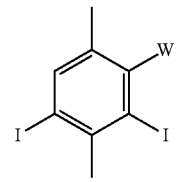
B

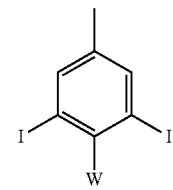
C

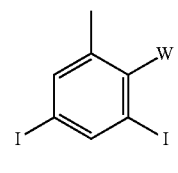
D

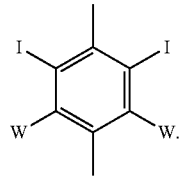
E

10. The polymer of claim 1 which is cross-linked.

11. The polymer of claim 1 in the form of a hydrogel comprising greater than 50% water wt/wt.

12. The polymer of claim 1 having an iodine content of greater than 10 mg iodine per $cm^3$ of fully hydrated polymer.

13. The polymer of claim 1 which has a radiodensity of greater than 500 HU.

14. The polymer of claim 1 which has a radiodensity of greater than 1000 HU.

15. The polymer of claim 1 which is substituted by groups, other than those in W, which are charged at pH 7.4.

16. A flowable composition comprising the polymer of claim 1.

17. A composition comprising the polymer of claim 1.

18. The composition comprising the polymer of claim 17, as a solution in either an aqueous solvent or organic solvent which is miscible with water.

19. The polymer of claim 1 in which p is 2 or 3.

* * * * *